(12) United States Patent
Kuczynski et al.

(10) Patent No.: US 7,608,112 B1
(45) Date of Patent: Oct. 27, 2009

(54) HIP ARTHROPLASTY TRIALING APPARATUS AND METHOD

(75) Inventors: John D. Kuczynski, Pequannock, NJ (US); Ormonde Mahoney, Athens, GA (US); Gautam N. Srivini, Hasbrouck Heights, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 720 days.

(21) Appl. No.: 10/939,820

(22) Filed: Sep. 13, 2004

(51) Int. Cl.
*A61F 2/32* (2006.01)

(52) U.S. Cl. .................. 623/22.11; 606/102; 623/22.42

(58) Field of Classification Search ........ 623/22–23.38; 606/102
See application file for complete search history.

(56) References Cited

U.S. PATENT DOCUMENTS

| | | | | |
|---|---|---|---|---|
| 3,102,536 A * | 9/1963 | Rose et al. | ................. | 623/22.4 |
| 4,566,448 A | 1/1986 | Rohr, Jr. | | |
| 4,693,724 A * | 9/1987 | Rhenter et al. | ........... | 623/22.44 |
| 4,892,546 A * | 1/1990 | Kotz et al. | ................ | 623/23.45 |
| 4,919,678 A | 4/1990 | Kranz | ..................... | 623/22.46 |
| 4,963,155 A * | 10/1990 | Lazzeri et al. | ............ | 623/22.42 |
| 5,116,338 A | 5/1992 | Poggie et al. | | |
| 5,213,112 A | 5/1993 | Niwa et al. | | |
| 5,507,830 A * | 4/1996 | DeMane et al. | .......... | 623/22.42 |
| 5,540,696 A | 7/1996 | Booth, Jr. et al. | | |
| 5,569,263 A | 10/1996 | Hein | | |
| 5,800,554 A | 9/1998 | Scholz | | |
| 5,876,459 A * | 3/1999 | Powell | ..................... | 623/23.15 |
| 5,906,644 A * | 5/1999 | Powell | ..................... | 623/20.15 |
| 5,911,723 A | 6/1999 | Ashby et al. | | |
| 6,136,036 A * | 10/2000 | Scholz | ..................... | 623/23.11 |
| 6,197,065 B1 | 3/2001 | Martin et al. | | |
| 6,299,648 B1 * | 10/2001 | Doubler et al. | .......... | 623/23.18 |
| 6,432,110 B1 * | 8/2002 | Richelsoph | ................... | 606/62 |
| 6,692,530 B2 * | 2/2004 | Doubler et al. | .......... | 623/22.42 |
| 6,746,487 B2 * | 6/2004 | Scifert et al. | ............. | 623/22.12 |
| 7,338,499 B1 * | 3/2008 | Kuczynski et al. | .......... | 606/102 |
| 2005/0043811 A1 * | 2/2005 | Doubler et al. | .......... | 623/22.42 |

OTHER PUBLICATIONS

Keggi Orthopaedic Foundation, Yale Univ. School of Med. Dept. of Orthopaedics & Rehab. Total Hip Arthroplasty Using the Minimally Invasive Anterior Surgical Approach, undated.

Stryker Howmedica Osteonics. "Surgical Technique, Achieving Perfect Balance, Accolade," undated.

\* cited by examiner

*Primary Examiner*—Eduardo C Robert
*Assistant Examiner*—Mary Hoffman
(74) *Attorney, Agent, or Firm*—Arthur Jacob (57) ABSTRACT

A femoral head offset and neck length required in a femoral component to be engaged with an acetabular component are determined for establishing appropriate hip mechanics in a prosthetic hip joint. Alternate selected sleeves of different lengths are interposed between a trial femoral head component and a trial femoral stem component movable relative to one another to admit each selected sleeve, interoperatively, for serial trialing to determine an appropriate trial distance, the appropriate trial distance corresponding to the required femoral head offset and neck length in the prosthetic hip joint.

13 Claims, 6 Drawing Sheets

HIP ARTHROPLASTY TRIALING APPARATUS AND METHOD

BACKGROUND OF THE INVENTION

1. Field of the Invention

The present invention relates generally to hip arthroplasty and pertains, more specifically, to apparatus and method for conducting interoperative trialing to determine an appropriate head offset and neck length in the femoral component of a prosthetic hip joint.

2. Description of the Related Prior Art

Total hip arthroplasty requires the preparation of an implant site for the reception of a femoral component and an acetabular component of a prosthetic hip joint to be implanted at the implant site. Proper hip mechanics are achieved through the selection of an appropriate head offset and neck length in the femoral component of the prosthetic hip implant. That is, the distance between the stem of the femoral component and the femoral head of the component, provided by the length of the neck of the component, establishes the requisite head offset and neck length which, in turn, provides the desired range of motion, leg length, and tension in the soft tissue at the implant site. Accordingly, of utmost importance is the ability to determine the appropriate neck length with precision, and to do so with ease and assurance.

The appropriate length required for the neck of a femoral component is determined once the size of each of the femoral component and the acetabular component is selected, and the implant site is prepared for the reception of each selected component. A preliminary assessment can be made utilizing radiographic analysis; however, a final determination usually is accomplished during the course of the implant procedure itself, that is, interoperatively.

In a current trialing procedure, serial trial prostheses are used to determine the appropriate neck length during the conduct of total hip arthroplasty. Thus, a provisional trial prosthesis is put into place, the hip joint is reduced, and the leg of the patient is moved by a surgeon through a range of motion to determine hip mechanics by hand. The trialing procedure requires that the trial prosthesis be removed and replaced with another in a series of trial prostheses in order to evaluate the effect of different neck lengths on hip mechanics. To achieve correct hip mechanics, a surgeon may need to perform several iterations, each requiring replacement of one trial prosthesis with another in the series, reduction of the hip joint, movement through a range of motion, and then dislocation of the joint again in order to change trials. The procedure can be quite time-consuming and even physically challenging, especially with larger patients. Moreover, the procedure is not suited to the conduct of more recently developed minimally invasive total hip arthroplasty where access to the hip joint is more limited.

BRIEF SUMMARY OF THE INVENTION

The present invention provides apparatus and method by which the appropriate head offset and neck length in a femoral component of a prosthetic hip joint is determined interoperatively with ease and with accuracy, for accomplishing optimal hip mechanics. As such, the present invention attains several objects and advantages, some of which are summarized as follows: Facilitates an interoperative determination of the appropriate head offset and neck length for a femoral component in a total hip arthroplasty; enables relatively quick and effective interoperative trialing for evaluation of hip mechanics at a prosthetic hip implant site; allows selective changes in the distance between the femoral stem of a femoral trial for a prosthetic hip joint and a femoral head of the femoral trial for interoperatively determining an appropriate head offset and neck length in the femoral component of the prosthetic hip joint itself, without the necessity for serial replacements of the entire trial and concomitant multiple dislocations of the hip joint; enables interoperative evaluation of hip mechanics at a hip implant site for consistent, precise results attained with ease and in less time; improves accuracy in the completion of a total hip arthroplasty; facilitates the conduct of minimally invasive total hip arthroplasty, where access to the hip joint is more limited; reduces pain and discomfort, as well as recovery time, in patients subjected to total hip arthroplasty.

The above objects and advantages, as well as further objects and advantages, are attained by the present invention which may be described briefly as apparatus for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the apparatus comprising: a connecting arrangement connecting the trial femoral head component with the trial femoral stem component for selective movement relative to one another, during the trialing procedure, along the predetermined direction for establishing a trial hip joint having a selected trial distance between the trial femoral head component and the trial femoral stem component; and a spacer for interposition between the trial femoral head component and the trial femoral stem component to maintain the selected trial distance between the trial femoral head component and the trial femoral stem component during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint.

The invention further provides a method for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the method comprising: connecting the trial femoral head component with the trial femoral stem component for selective trialing movement relative to one another, during the trialing procedure, along the predetermined direction; moving the trial femoral head component and the trial femoral stem component relative to one another, during the trialing procedure, along the predetermined direction of movement for establishing a trial hip joint having a selected trial distance between the trial femoral head component and the trial femoral stem component; and interposing a spacer between the trial femoral head component and the trial femoral stem component to maintain the selected trial distance between the trial femoral head component and the trial femoral stem component during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint.

BRIEF DESCRIPTION OF THE SEVERAL VIEWS OF THE DRAWING

The invention will be understood more fully, while still further objects and advantages will become apparent, in the following detailed description of preferred embodiments of the invention illustrated in the accompanying drawing, in which.

DETAILED DESCRIPTION OF THE INVENTION

Figures 1, 2:
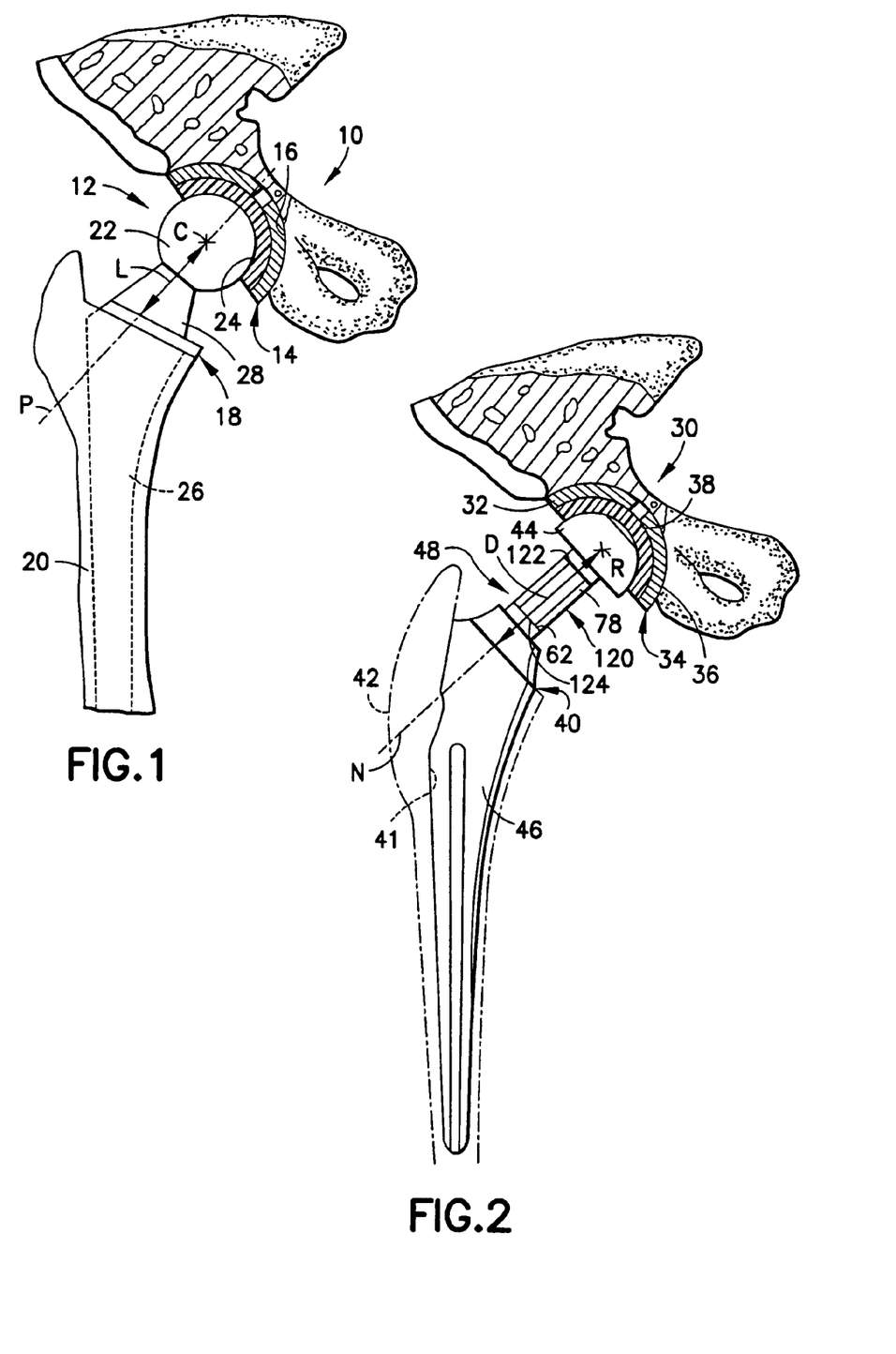
FIG. 1 is a pictorial illustration, somewhat diagrammatic, of a prosthetic hip joint implanted at an implant site.
FIG. 2 is a pictorial illustration, somewhat diagrammatic, of apparatus constructed in accordance with the present invention, in place at an implant site during trialing in connection with the conduct of a total hip arthroplasty.

Referring now to the drawing, and especially to FIG. 1 thereof, an implant site 10 has been provided with a prosthetic hip joint 12 which is seen to include an acetabular component 14 implanted in acetabulum 16, and a femoral component 18 implanted in proximal femur 20. Femoral component 18 includes a femoral head 22, which is engaged with a bearing surface 24 of the acetabular component 14 for articulation of the prosthetic hip joint 12, a femoral stem 26, which is affixed within the proximal femur 20 to secure the femoral component 18 in place, and a femoral neck 28, which connects the femoral head 22 to the femoral stem 26 and which spaces the femoral head 22 from the femoral stem 26, all as now well-known in prosthetic hip joints.

As is conventional, prosthetic hip joint 12 relies upon soft tissue (not shown) at the implant site 10 to maintain femoral head 22 of femoral component 18 appropriately engaged with bearing surface 24 of acetabular component 14 for proper hip mechanics at the hip joint 12. The attainment of requisite appropriate hip mechanics, including range of motion, leg length and tension in the soft tissue, is dependent upon the distance between the femoral head 22 and the femoral stem 26 provided by the femoral neck 28, as represented by the length L which extends along a predetermined direction P between the center of rotation C of femoral head 22 and the femoral stem 26. The desired hip mechanics are attained by selecting an appropriate length L. Accordingly, in order to optimize hip mechanics, length L be selected with precision.

Turning now to FIG. 2, an implant site 30 has been prepared for a prosthetic hip implant during the course of a total hip arthroplasty. Acetabulum 32 has been provided with an acetabular trial, shown in the form of acetabular trial 34 including a trial acetabular shell 36 placed within the acetabulum 32 and a trial bearing 38 seated within the trial acetabular shell 36. A femoral trial 40 has been placed within a prepared cavity 41 in proximal femur 42 and includes a trial femoral head component 44 shown, in a diagrammatic illustration, engaged within trial bearing 38, and a trial femoral stem component 46, all simulating, in a trial hip joint 48, the engagement of a femoral component with an acetabular component of a prosthetic hip joint to be implanted at the implant site 30. The attainment of appropriate hip mechanics upon completion of the total hip arthroplasty is a function of head offset and neck length in the femoral component of the prosthetic hip joint implanted at the implant site 30. Accordingly, it becomes of utmost importance that the head offset and neck length be determined with accuracy.

The distance between the center of rotation R of trial femoral head component 44 and the trial femoral stem component 46 of femoral trial 40, as shown at a trial distance D, along predetermined direction N, corresponds to the head offset and neck length desired in the femoral component of the prosthetic hip joint to be implanted at the implant site 30, as illustrated by way of example as length L along predetermined direction P in femoral component 18 of FIG. 1. A change in the distance D results in a corresponding change in the head offset and neck length, and a concomitant change in the hip mechanics as simulated by the trial femoral head component 44 and the trial bearing 38. The present invention provides for selective changes in distance D, interoperatively, so as to attain optimal hip mechanics through establishing a requisite neck length in the femoral trial 40.

Figure 3:
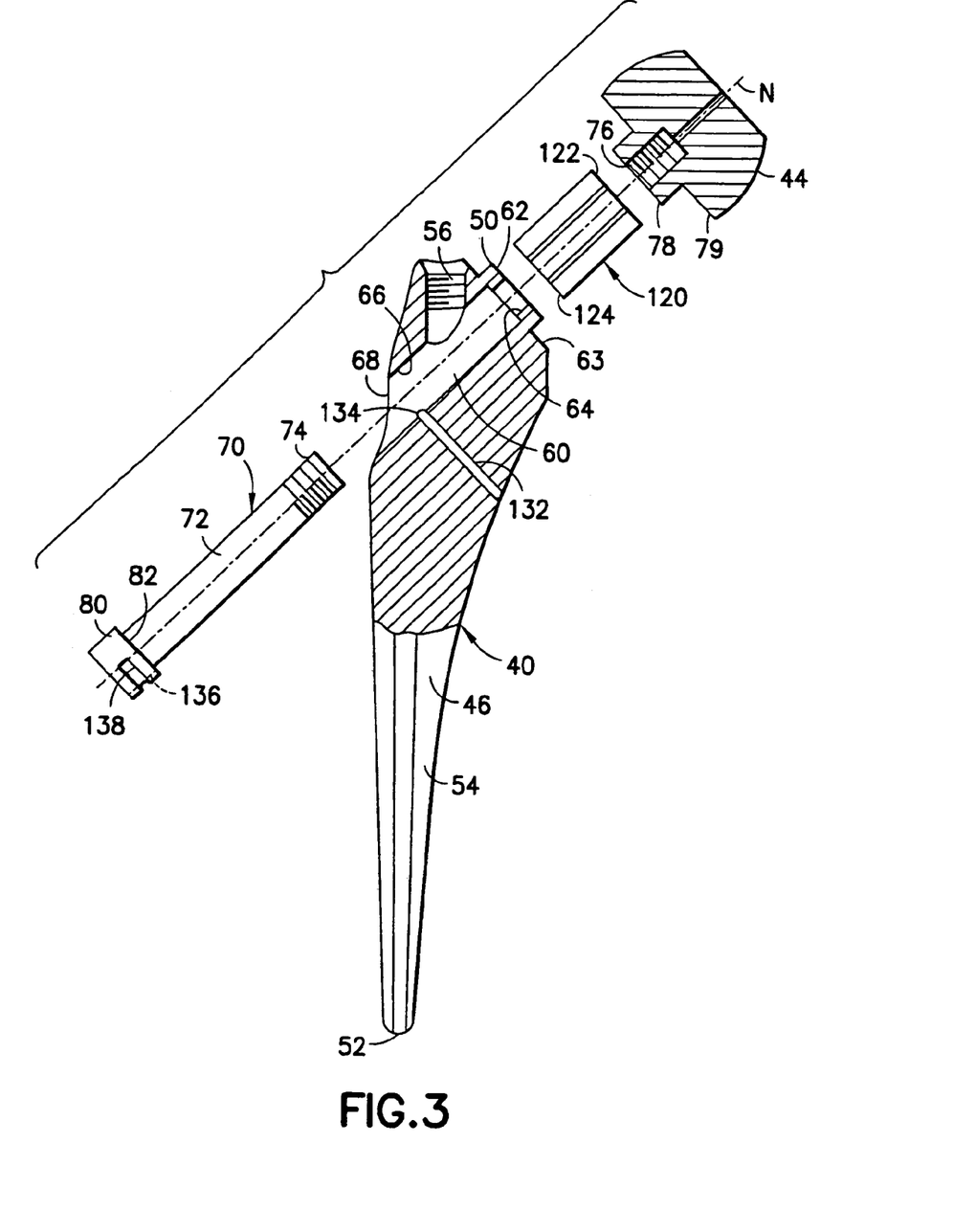
FIG. 3 is an enlarged exploded perspective view of the apparatus.

Referring now to FIGS. 3 through 7, as well as to FIG. 2, the trial femoral stem component 46 of femoral trial 40 extends between a proximal end 50 and a distal end 52. A stem 54 extends from the distal end 52 toward the proximal end 50, and, as best seen in FIG. 3, a threaded hole 56 extends into the trial femoral stem component 46 adjacent the proximal end 50, for purposes to be described below. The trial femoral head component 44 is connected with the trial femoral stem component 46 with a connecting arrangement which includes a passage shown in the form of cylindrical bore 60 extending through the femoral trial stem component 46, along the predetermined direction N, from a first reference surface, in the form of stem reference surface 62 at the proximal end 50. A stem engagement surface 63 is spaced distally from the stem reference surface 62, for purposes to be described below. Bore 60 includes a smaller diameter portion 64, adjacent stem reference surface 62, and a larger diameter portion 66 extending along direction N from the smaller diameter portion 64 to an opening 68.

A trial neck 70 includes a shaft 72 extending longitudinally along an intermediate portion of the trial neck 70, the shaft 72 being dimensioned and configured for longitudinal sliding engagement within bore 60 so that the trial neck 70 is movable relative to the trial femoral stem component 46 in longitudinal directions along predetermined direction N. A threaded post 74 extends longitudinally along a proximal portion of the trial neck 70, and a threaded socket 76 extends longitudinally into femoral head component 44. A second reference surface in the form of a head reference surface 78 extends laterally across the femoral head component 44, and a head engagement surface 79 is spaced proximally from the head reference surface 78, for purposes to be described below. With shaft 72 inserted through opening 68 to pass through bore 60, selected trial femoral head component 44 is threaded onto threaded post 74 and, by virtue of the securement of femoral head component 44 on post 74, and a collar 80 at the distal end of shaft 72 providing a laterally extending shoulder 82 adjacent the distal end of shaft 72, collar 80 having a diameter essentially complementary to larger diameter portion 66 of bore 60 and larger than smaller diameter portion 64 of bore 60, trial neck 70 is captured in femoral trial stem component 46. The diameter of collar 80, being essentially complementary to larger diameter portion 66 of bore 60, enables the captured trial neck 70 to slide within bore 60, along the predetermined direction N, for selectively changing the distance D, as will now be described.

Figures 4, 5:
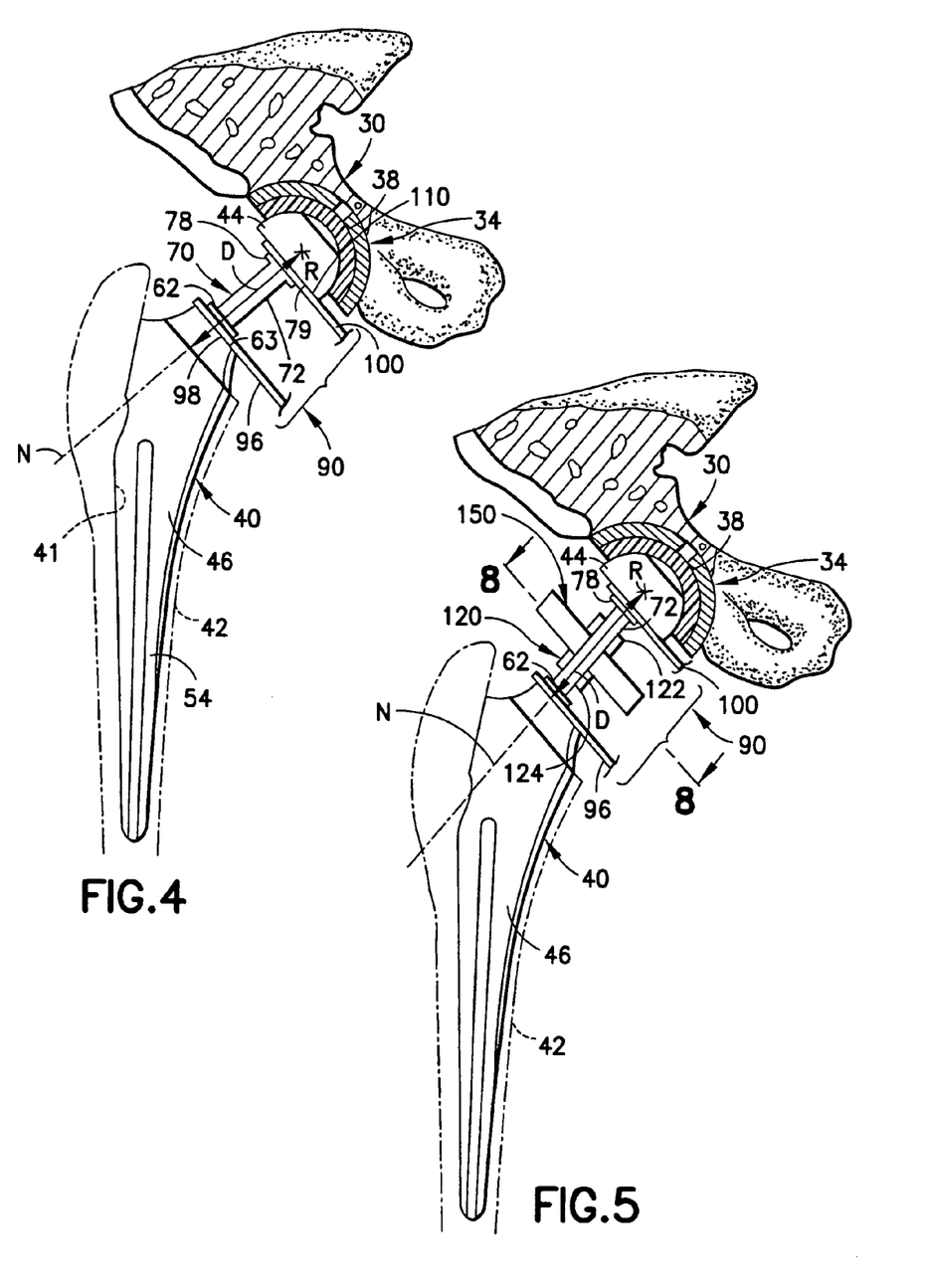
FIG. 4 is a pictorial illustration, somewhat diagrammatic, showing the apparatus in use in a trialing procedure conducted in accordance with a method of the present invention.
FIG. 5 is a pictorial illustration similar to FIG. 4 and showing another step in the trialing procedure.

Femoral trial 40 is assembled for use by inserting shaft 72 of trial neck 70 through bore 60 of trial femoral stem component 46, and threading trial femoral head component 44 onto threaded post 74 of trial neck 70. Stem 54 then is inserted into prepared cavity 41 in proximal femur 42, as seen in FIG. 4, using conventional techniques, and the hip joint is reduced to place the trial femoral head component 44 into engagement with the trial bearing 38 of the acetabular trial 34, as illustrated in FIG. 4. Once the trial femoral head component 44 is seated within the trial bearing 38, a spreader, shown diagrammatically at 90, is engaged with the femoral trial 40 for selectively changing the distance D between the trial femoral head component 44 and the trial femoral stem component 46 of femoral trial 40.

Referring now to FIG. 5, as well as to FIG. 4, spreader 90 includes a first arm 96 having a first engagement face 98 and a second arm 100 having a second engagement face 110. As seen in FIG. 4, spreader 90 is coupled with femoral trial 40 by engaging the first engagement face 98 with the stem engagement surface 63 on the trial femoral stem component 46, thereby coupling the first arm 96 with the trial femoral stem component 46, and by engaging the second engagement face 110 with the head engagement surface 79 on the femoral head component 44, thereby coupling the second arm 100 with the trial femoral head component 44 while leaving the stem reference surface 62 and the head reference surface 78 exposed, for purposes described below.

With the spreader 90 coupled to the femoral trial 40, and with the femoral trial 40 engaged with the acetabular trial 34, as seen in FIG. 4, the first and second arms 96 and 100 are moved away from one another to increase the distance D, along the predetermined direction N, by virtue of the sliding engagement between the shaft 72 and the bore 60. A selected spacer, shown in FIG. 3 in the form of a sleeve 120, then is interposed between the trial femoral head component 44 and the trial femoral stem component 46 to maintain a selected trial distance between the trial femoral head component 44 and the trial femoral stem component 46 during subsequent interoperative trialing to evaluate hip mechanics, as will be described in detail below.

Figures 6, 7, 8:
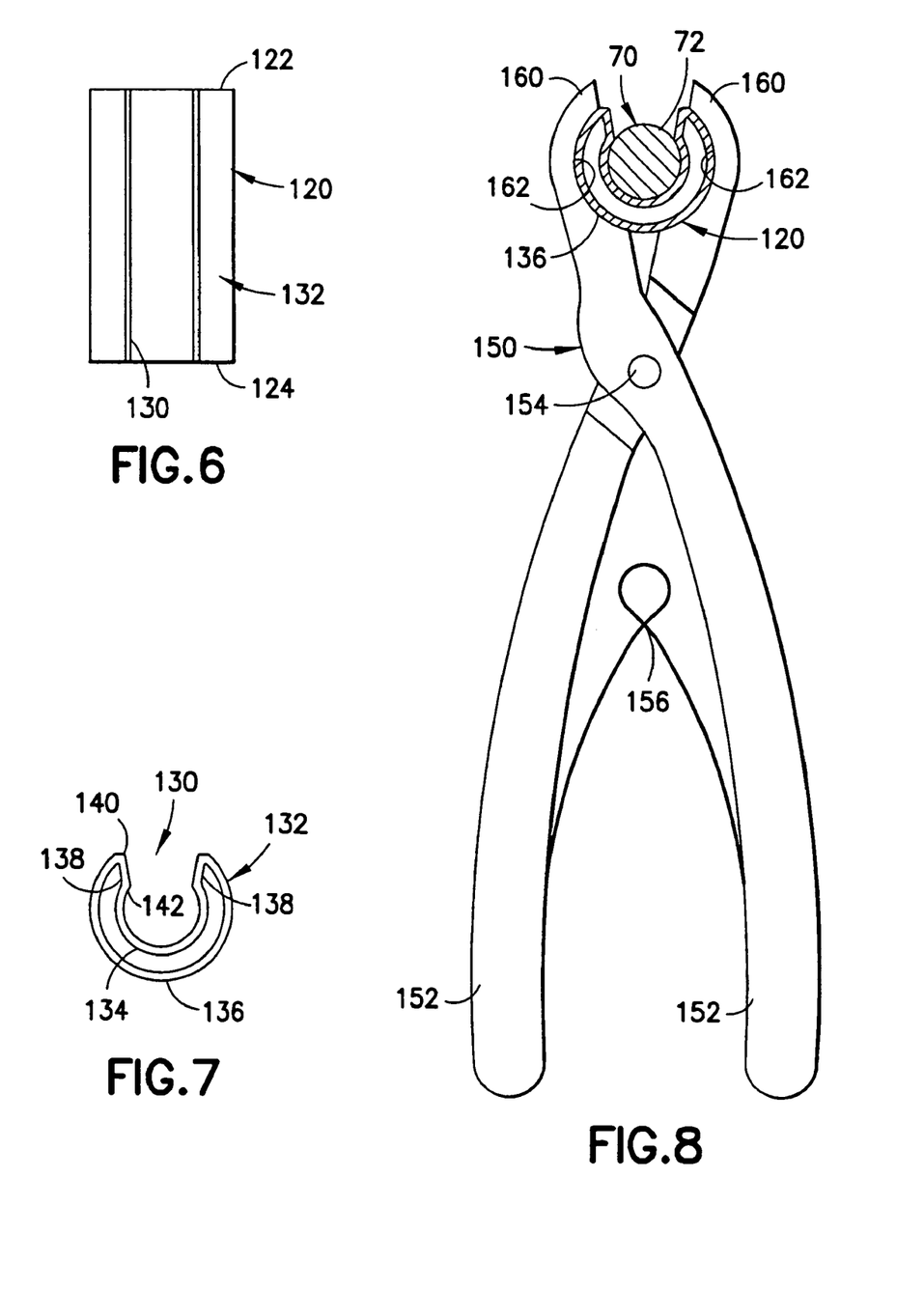
FIG. 6 is an enlarged front elevational view of a component part of the apparatus in the form of a sleeve.
FIG. 7 is an end view of the sleeve of FIG. 6.
FIG. 8 is an enlarged, cross-sectional view taken along line 8-8 of FIG. 5.

With the sleeve 120 in place between the trial femoral head component 44 and the trial femoral stem component 46, the hip joint is reduced by removing spreader 90. As best seen in FIGS. 6 and 7, sleeve 120 has a generally cylindrical configuration and extends longitudinally between a proximal end 122 and a longitudinally opposite distal end 124. With the sleeve 120 in place and the spreader 90 removed, proximal end 122 of sleeve 120 engages head reference surface 78 of the trial femoral head component 44, and distal end 124 engages stem reference surface 62 of the trial femoral stem component 46 so that an accurate distance, equivalent to the longitudinal length of sleeve 120 between opposite ends 122 and 124, is maintained in the reduced hip joint, as seen in FIG. 2. Evaluation of the hip mechanics then is accomplished by articulating the hip joint through a full range of motion, and checking for appropriate leg length and tension.

Sleeve 120 is interposed between the trial femoral head component 44 and the trial femoral stem component 46 by moving the sleeve 120 laterally over the intermediate portion of the trial neck 70 until the sleeve 120 is seated on the shaft 72. To this end, sleeve 120 is split longitudinally by a breach 130 in the wall 132 of the sleeve 120, so that the wall 132 has a generally C-shaped lateral cross-sectional configuration, as seen in FIGS. 7 and 8. Wall 132 is hollow, that is, an inner wall portion in the form of an inner band 134 is spaced radially from an outer wall portion in the form of an outer band 136, the bands 134 and 136 being joined by transverse wall portions in the form of wall segments 138 extending along the breach 130 to form an integrated tubular wall structure. The inner band 134 has a contour configuration dimensioned and configured for fitting over the shaft 72 to seat the sleeve 120 on the shaft 72, and the breach 130 is tapered from a larger opening 140 at the outer band 136 to a smaller opening 142 at the inner band 134 to facilitate lateral movement of the sleeve 120 over the shaft 72. The bands 134 and 136 preferably are constructed of a resiliently flexible material, such as a biocompatible metal alloy, so that the sleeve 120 flexes radially to enable the sleeve 120 to pass over the shaft 72 and then be captured in place on the shaft 72. In the illustrated preferred embodiment, shaft 72 has a circular cross-sectional configuration and the C-shaped cross-sectional configuration of the sleeve 120 allows the sleeve 120 to be snapped over the shaft 72 and held in place. The ends 122 and 124 of the sleeve 120 are open between the bands 134 and 136 so as not to impede resilient flexing of the bands 134 and 136. In addition, the open ends 122 and 124 permit the circulation of cleaning media for accomplishing sterilization of the sleeve 120 for use.

As best seen in FIGS. 5 and 8, a spacer tool 150 is utilized for installing the sleeve 120 on the shaft 72 of the trial neck 70. Tool 150 includes actuator handles 152 pivoted at a pivot pin 154 and biased away from one another by a spring mechanism 156. Each actuator handle 152 carries a jaw 160, and jaws 160 are opposed to one another, with the pivot pin 154 located intermediate each handle 152 and a corresponding jaw 160 so that the jaws 160 are biased away from one another by the spring mechanism 156. The jaws 160 each include an inner jaw surface 162 having a surface contour configured and dimensioned for selectively encircling and gripping sleeve 120 along the outer band 136, while maintaining access to breach 130. Installation of the sleeve 120 on the shaft 72, for interposition of the sleeve 120 between the trial femoral head component 44 and the trial femoral stem component 46, is accomplished by grasping the actuator handles 152, moving the jaws 160 over the sleeve 120, and then actuating the handles 152 to grip the sleeve 120 between the jaws 160.

The sleeve 120 then is juxtaposed with the intermediate portion of the trial neck 70, with the breach 130 confronting the shaft 72, and is moved laterally until the shaft 72 passes through the breach 130 and is seated within the inner band 134 of the sleeve 120, as seen in FIGS. 5 and 8. The first and second arms 96 and 100 of spreader 90 are moved toward one another until the ends 122 and 124 of sleeve 120 are engaged with the respective exposed head reference surface 78 and stem reference surface 62. The spreader 90 then is uncoupled from femoral trial 40 and the tool 150 is removed from the sleeve 120 by merely opening the jaws 160.

Removal of the sleeve 120 from the trial neck 70 is accomplished by reversal of the above-described installation procedure. Jaws 160 are engaged with the outer band 136 of the sleeve 120, as seen in FIG. 8, and held in such engagement while the tool 150 is pulled laterally away from the trial neck 70, flexing the wall 132 of the sleeve 120 and releasing the sleeve 120 from the shaft 72.

Figure 9:
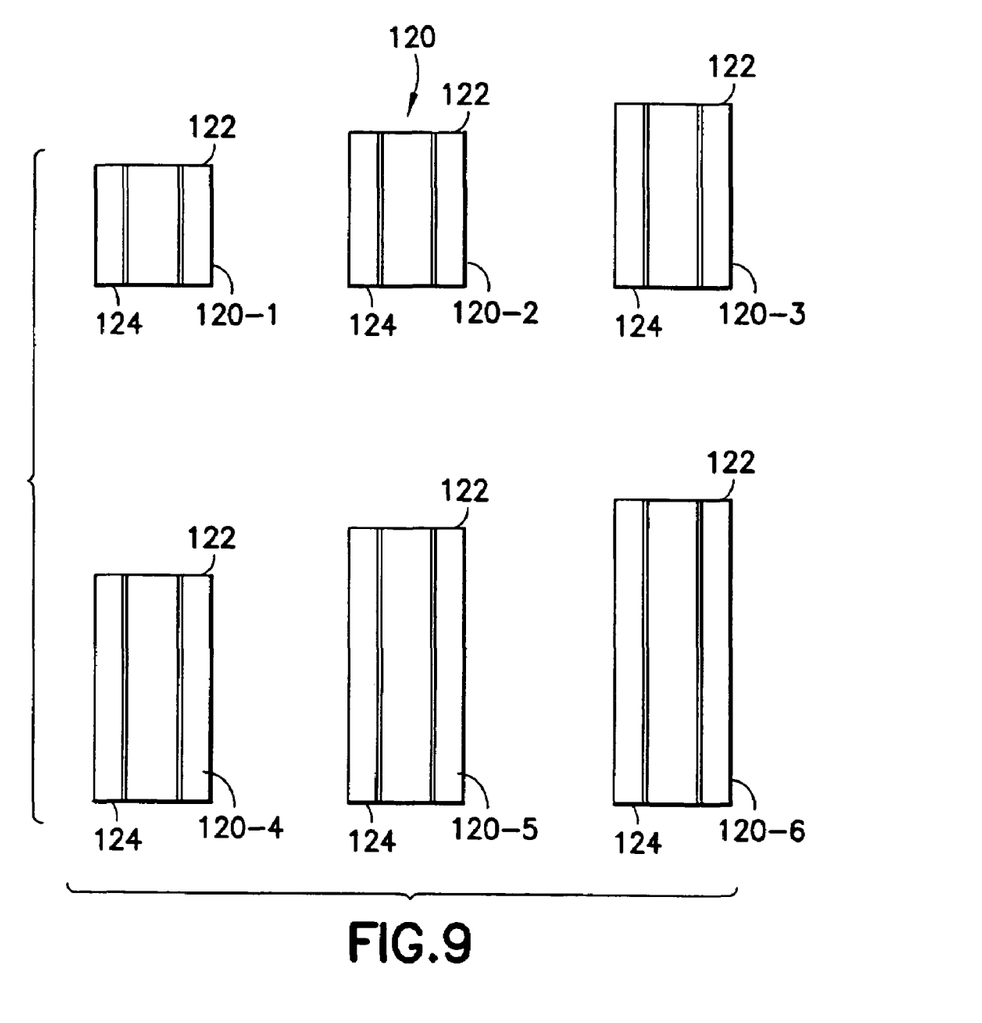
FIG. 9 is an elevational view of further component parts of the apparatus.

During the course of the trialing procedure, sleeve 120 can be interchanged with other sleeves having different lengths, enabling the evaluation of the effect of different distances D on the hip mechanics provided at the trial hip joint 48 and enabling the determination of an appropriate distance D. Thus, as seen in FIG. 9, a plurality of sleeves 120 is illustrated, in the form of sleeves 120-1, 120-2, 120-3, 120-4, 120-5 and 120-6, each having a different longitudinal length between opposite ends 122, and 124. Each sleeve 120-1 through 120-6 is constructed similar to sleeve 120, that is, each has the same diameter and the same breach as described above in connection with sleeve 120, enabling the installation of any one of these sleeves utilizing tool 150 as described above. In this manner, the trialing procedure is continued by the selection and installation of alternate sleeves for serial evaluations until appropriate hip mechanics are attained. The distance D at which the appropriate hip mechanics are attained is recorded and is used as a basis for the choice of head offset and neck length in the femoral component of the prosthetic hip joint to be implanted at implant site 30.

Unlike conventional trialing procedures in which the hip joint is repeatedly dislocated and reduced with the insertion and extraction of alternate femoral trials, the several iterations conducted in the trialing procedure of the present invention merely require the insertion and removal of only alternate sleeves 120, without repeated dislocations and reductions of the hip joint. Moreover, soft tissue damage is avoided by the ability to retract the trial femoral head component 44 toward the trial femoral stem component 46, in the absence of any sleeve 120, so as to collapse the femoral trial 40 into a relatively compact configuration during both insertion and extraction of the femoral trial 40.

In the preferred embodiment illustrated by femoral trial 40, a locking mechanism selectively secures the trial femoral head component 44 in a fixed position relative to trial femoral stem component 46, preferably closely adjacent the trial femoral stem component 46, to establish a collapsed, compact configuration for facilitating insertion and extraction of femoral trial 40 and avoiding soft tissue damage during such insertion and extraction. Thus, with reference to FIGS. 10 through 12, as well as to FIG. 3, a locking mechanism 130 is seen to include a locking pin 132 affixed within stem 54 of trial femoral stem component 46 and extending into bore 60 at tip 134 of locking pin 132. A longitudinal groove 136 extends along the length of collar 80, and a transverse groove 138 intersects longitudinal groove 136 and extends circumferentially along a portion of the periphery of collar 80. Grooves 136 and 138 are dimensioned and configured to admit the tip 134 of locking pin 132 for sliding movement within either of the grooves 136 and 138.

Figures 10, 11, 12:
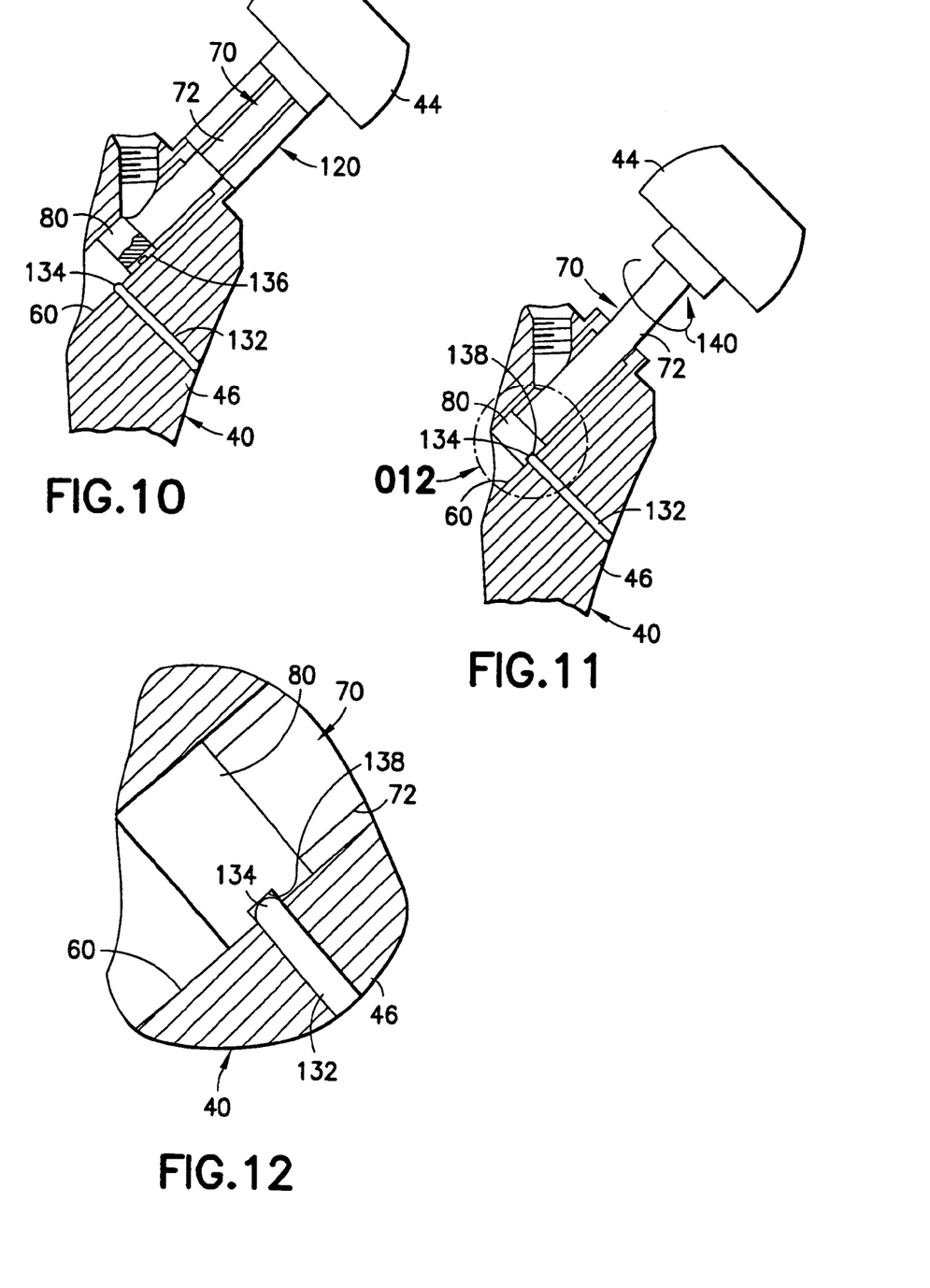
FIG. 10 is an enlarged, fragmentary longitudinal cross-sectional view of a portion of FIG. 2.
FIG. 11 is an enlarged, fragmentary longitudinal cross-sectional view similar to FIG. 10, and showing component parts in another position.
FIG. 12 is a further enlarged view of a portion of FIG. 11 indicated by the circled area 012 in FIG. 11.

Upon alignment of longitudinal groove 136 with tip 134 of locking pin 132, as seen in FIG. 10, as well as in FIG. 3, shaft 72 is free to slide within bore 60 for locating trial femoral head component 44 at a selected distance D relative to trial femoral stem component 46, as determined by the placement of a selected sleeve 120 upon shaft 72, as described above. However, upon registration of transverse groove 138 with tip 134 of locking pin 132, and turning shaft 72 about direction N, as illustrated by arrow 140 in FIG. 11, tip 134 of locking pin 132 will enter transverse groove 138, as seen in FIGS. 11 and 12, to preclude longitudinal movement of shaft 72, along direction N, thereby locking trial femoral head component 44 in a fixed position relative to trial femoral stem component 46. In this manner, any sliding movement of shaft 72 and concomitant movement of trial femoral head component 44 relative to trial femoral stem component 46 is precluded, facilitating manipulation of femoral trial 40 during insertion and extraction. Once femoral trial 40 is in place in proximal femur 42, trial femoral head component 44 merely is rotated, along with shaft 72, about direction N, to once again align longitudinal groove 136 with tip 134 of locking pin 132 and thereby release shaft 72 for longitudinal movement, allowing selected changes in distance D, as described above.

The procedure is quick and accurate, and is conducted readily in connection with minimally invasive surgical procedures in which access to the hip joint is limited, since alternate sleeves 120 are passed through smaller incisions with relative ease and there is no requirement to pass a trial femoral head and trial femoral neck to the joint with each iteration. In addition, the collapsed, compact configuration of femoral trial 40, available during insertion and extraction of the femoral trial 40, facilitates the passing of femoral trial 40 through smaller incisions.

Subsequent to determining the appropriate head offset and neck length, the joint is dislocated and the femoral trial 40 is extracted, with the assistance of a conventional extraction instrument which can be coupled to the threaded hole 56 of the trial femoral stem component 46. An appropriate acetabular component and femoral component then are implanted at the implant site 30. Ultimately, an appropriate femoral head prosthesis is assembled with the implanted femoral stem component, the joint is reduced, and a final range of motion and tension evaluation is conducted manually, prior to completion of the implant procedure.

It will be seen that the present invention attains the several objects and advantages summarized above, namely: Facilitates an interoperative determination of the appropriate head offset and neck length for a femoral component in a total hip arthroplasty; enables relatively quick and effective interoperative trialing for evaluation of hip mechanics at a prosthetic hip implant site; allows selective changes in the distance between the femoral stem of a femoral trial for a prosthetic hip joint and a femoral head of the femoral trial for interoperatively determining an appropriate head offset and neck length in the femoral component of the prosthetic hip joint itself, without the necessity for serial replacements of the entire trial and concomitant multiple dislocations of the hip joint; enables interoperative evaluation of hip mechanics at a hip implant site for consistent, precise results attained with ease and in less time; improves accuracy in the completion of a total hip arthroplasty; facilitates the conduct of minimally invasive total hip arthroplasty, where access to the hip joint is more limited; reduces pain and discomfort, as well as recovery time, in patients subjected to total hip arthroplasty.

It is to be understood that the above detailed description of preferred embodiments of the invention are provided by way of example only. Various details of design, construction and procedure may be modified without departing from the true spirit and scope of the invention, as set forth in the appended claims.

The embodiments of the invention in which an exclusive property or privilege is claimed are defined as follows:

1. Apparatus for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the apparatus comprising:
   a connecting arrangement connecting the trial femoral head component with the trial femoral stem component for selective movement relative to one another through trial distances between the trial femoral head component and the trial femoral stem component, the connecting arrangement being dimensioned and configured for enabling the selective movement during the trialing procedure, along the predetermined direction, while the trial femoral head component and the trial femoral stem component remain connected to one another at the implant site for establishing a trial hip joint having a selected trial distance between the trial femoral head component and the trial femoral stem component while the trial femoral head component and the trial femoral stem component remain connected to one another at the implant site; and
   a spacer dimensioned and configured for interposition between the trial femoral head component and the trial femoral stem component while the trial femoral head component and the trial femoral stem component remain connected to one another at the implant site so as to enable the selected trial distance between the trial femoral head component and the trial femoral stem component to be maintained during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint; and wherein
   the connecting arrangement includes:
   a trial femoral neck component for assembly with the trial femoral head component, the trial femoral neck component including a shaft; and
   a passage in the trial femoral stem component, the passage being dimensioned and configured for receiving the shaft for sliding motion enabling movement of the trial femoral head component and the trial femoral stem component relative to one another; and
   the spacer includes a sleeve having a prescribed longitudinal length, the sleeve being split along the length thereof to enable selective lateral placement of the sleeve over the shaft for spacing the trial femoral head component from the trial femoral stem component according to the prescribed length of the sleeve.

2. Apparatus for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the apparatus comprising:
   a connecting arrangement connecting the trial femoral head component with the trial femoral stem component for selective movement relative to one another during the trialing procedure, along the predetermined direction for establishing a trial hip joint having a selected trial distance between the trial femoral head component and the trial femoral stem component, the connecting arrangement including a trial femoral neck component for assembly with the trial femoral head component, the trial femoral neck component including a shaft, and a passage in the trial femoral stem component, the passage being dimensioned and configured for receiving the shaft for sliding motion enabling movement of the trial femoral head component and the trial femoral stem component relative to one another; and
   a spacer for interposition between the trial femoral head component and the trial femoral stem component to maintain the selected trial distance between the trial femoral head component and the trial femoral stem component during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint, the spacer including a sleeve having a prescribed longitudinal length, the sleeve being split along the length thereof to enable selective lateral placement of the sleeve over the shaft for spacing the trial femoral head component from the trial femoral stem component according to the prescribed length of the sleeve, the sleeve being one of a plurality of sleeves, each sleeve of the plurality of sleeves having a length different from other sleeves of the plurality of sleeves, each sleeve being selectable for interposition between the trial femoral head component and the trial femoral stem component to maintain a corresponding selected trial distance between the trial femoral head component and the trial femoral stem component during subsequent corresponding serial interoperative trialing to determine the appropriate trial distance.

3. The apparatus of claim 1 wherein:
   the sleeve includes longitudinally opposite first and second ends;
   the trial femoral stem component includes a first reference surface for engagement by the first end of the sleeve upon interposition of the sleeve between the trial femoral head component and the trial femoral stem component; and
   the trial femoral head component includes a second reference surface for engagement by the second end of the sleeve upon interposition of the sleeve between the trial femoral head component and the trial femoral stem component.

4. The apparatus of claim 1 wherein the sleeve includes a generally C-shaped lateral cross-sectional configuration.

5. The apparatus of claim 1 wherein the sleeve includes an inner wall portion and an outer wall portion spaced laterally outwardly from the inner wall portion, the inner and outer wall portions being integrated into a tubular wall structure.

6. The apparatus of claim 5 wherein the tubular wall structure extends longitudinally between opposite ends and includes an opening between the inner and outer wall portions at each of the opposite ends.

7. The apparatus of claim 6 wherein the sleeve includes a generally C-shaped lateral cross-sectional configuration.

8. The apparatus of claim 1 including a locking mechanism for selectively securing the trial femoral head component against movement relative to the trial femoral stem component.

9. Apparatus for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the apparatus comprising:
 a connecting arrangement connecting the trial femoral head component with the trial femoral stem component for selective movement relative to one another during the trialing procedure, along the predetermined direction for establishing a trial hip joint having a selected trial distance between the trial femoral head component and the trial femoral stem component;
 a spacer for interposition between the trial femoral head component and the trial femoral stem component to maintain the selected trial distance between the trial femoral head component and the trial femoral stem component during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint; and
 a locking mechanism for selectively securing the trial femoral head component against movement relative to the trial femoral stem component; and wherein:
 the connecting arrangement includes:
 a trial femoral neck component for assembly with the trial femoral head component, the trial femoral neck component including a longitudinally extending shaft; and
 a longitudinally extending passage in the trial femoral stem component, the passage being dimensioned and configured for receiving the shaft for sliding motion enabling movement of the trial femoral head component and the trial femoral stem component relative to one another; and
 the locking mechanism includes:
 a locking pin extending into the passage, transverse to the passage;
 a collar on the shaft, the collar being dimensioned and configured for sliding along the passage with sliding movement of the shaft in longitudinal directions and for rotation with rotation of the shaft about a longitudinal direction;
 a longitudinal groove in the collar for selective alignment with the locking pin, the longitudinal groove being dimensioned and configured for permitting entry of the locking pin into the longitudinal groove for sliding movement of the collar along the passage in longitudinal directions; and
 a transverse groove in the collar, intersecting the longitudinal groove, the transverse groove being dimensioned and configured for permitting selective entry of the pin into the transverse groove, in response to registration of the transverse groove with the pin and rotation of the collar to admit the pin into the transverse groove, to preclude longitudinal sliding movement of the collar in the passage, thereby precluding longitudinal sliding movement of the shaft within the passage.

10. A method for interoperatively determining, during a trialing procedure conducted in connection with total hip arthroplasty at an implant site, a femoral head offset and neck length required in a femoral component to be engaged with an acetabular component in a prosthetic hip joint to be implanted at the implant site for establishing appropriate hip mechanics in the prosthetic hip joint, by determining a trial distance, along a predetermined direction, between a trial femoral head component and a trial femoral stem component of a femoral trial placed at the implant site with the trial femoral head component engaged with a trial acetabular component in a trial hip joint, the trial distance corresponding to the required femoral head offset and neck length in the prosthetic hip joint, the method comprising:
 connecting the trial femoral head component with the trial femoral stem component for selective trialing movement relative to one another through trial distances between the trial femoral head component and the trial femoral stem component, during the trialing procedure, along the predetermined direction, while the trial femoral head component and the trial femoral stem component remain connected to one another at the implant site;
 moving the trial femoral head component and the trial femoral stem component relative to one another while the trial femoral head component and the trial femoral stem component remain connected to one another at the implant site, during the trialing procedure, along the predetermined direction of movement for establishing a trial hip joint having a selected trial distance between the trial femoral head component and the trial femoral stem component; and
 interposing a spacer between the trial femoral head component and the trial femoral stem component, while the trial femoral head component and the trial femoral stem component remain connected to one another at the implant site, to maintain the selected trial distance between the trial femoral head component and the trial femoral stem component during subsequent interoperative trialing to evaluate hip mechanics in the trial hip joint, thereby determining interoperatively an appropriate trial distance, the appropriate trial distance corresponding to the femoral head offset and neck length required in the femoral component for establishing the appropriate hip mechanics in the prosthetic hip joint.

11. The method of claim 10 including selecting the spacer from a plurality of spacers having different lengths between longitudinally opposite ends, and serially interposing selected spacers to effect selected trial distances corresponding to each length between opposite ends of each selected spacer for corresponding serial trialing.

12. The method of claim 10 including locking the trial femoral head component against movement relative to the trial femoral stem component during placement of the femoral trial at the implant site, and then releasing the trial femoral head component for movement relative to the trial femoral stem component during the trialing procedure to determine the appropriate trial distance.

13. The method of claim 10 including locking the trial femoral head component against movement relative to the trial femoral stem component during extraction of the femoral trial from the implant site.

* * * * *